United States Patent [19]

Kato

[11] Patent Number: 4,872,029
[45] Date of Patent: Oct. 3, 1989

[54] AUTOMATIC ADJUSTED LIGHT SWITCHING CIRCUIT

[75] Inventor: Tadashi Kato, Hachioji, Japan

[73] Assignee: Olympus Optical Co., Ltd., Tokyo, Japan

[21] Appl. No.: 215,128

[22] Filed: Jul. 5, 1988

[30] Foreign Application Priority Data

Apr. 8, 1988 [JP] Japan .................................. 63-87519

[51] Int. Cl.$^4$ .............................................. G03G 7/08
[52] U.S. Cl. ..................................... 354/413; 354/62; 358/98; 128/6
[58] Field of Search ................. 354/413, 416, 417, 62, 354/63, 74, 76; 358/98, 909; 128/6-9

[56] References Cited

U.S. PATENT DOCUMENTS

| | | | |
|---|---|---|---|
| 4,475,541 | 10/1984 | Takamatsu et al. | 354/62 |
| 4,524,761 | 6/1985 | Hattori et al. | 354/62 |
| 4,561,429 | 12/1985 | Sato et al. | 354/62 |

Primary Examiner—L. T. Hix
Assistant Examiner—David M. Gray
Attorney, Agent, or Firm—Armstrong, Nikaido, Marmelstein, Kubovcik & Murray

[57] ABSTRACT

In this invention, an automatic adjusted light switching circuit which can feed an illuminating light to an endoscope is provided with a light source emitting an illuminating light to illuminate an object. The illuminating light has the light amount controlled by an iris driving circuit. An adjusted light controlling circuit for a still camera outputs a control signal controlling the iris driving circuit with a photometric signal. An adjusted light controlling circuit for a video camera outputs to the iris driving circuit a control signal for making a video signal of the most suitable brightness from a video signal obtained from a solid state imaging device imaging the object image. Either one of the control signals output by the adjusted light controlling circuit for the still camera and the adjusted light controlling circuit for the video camera is slected by a switching circuit and is input into the iris driving circuit.

6 Claims, 4 Drawing Sheets

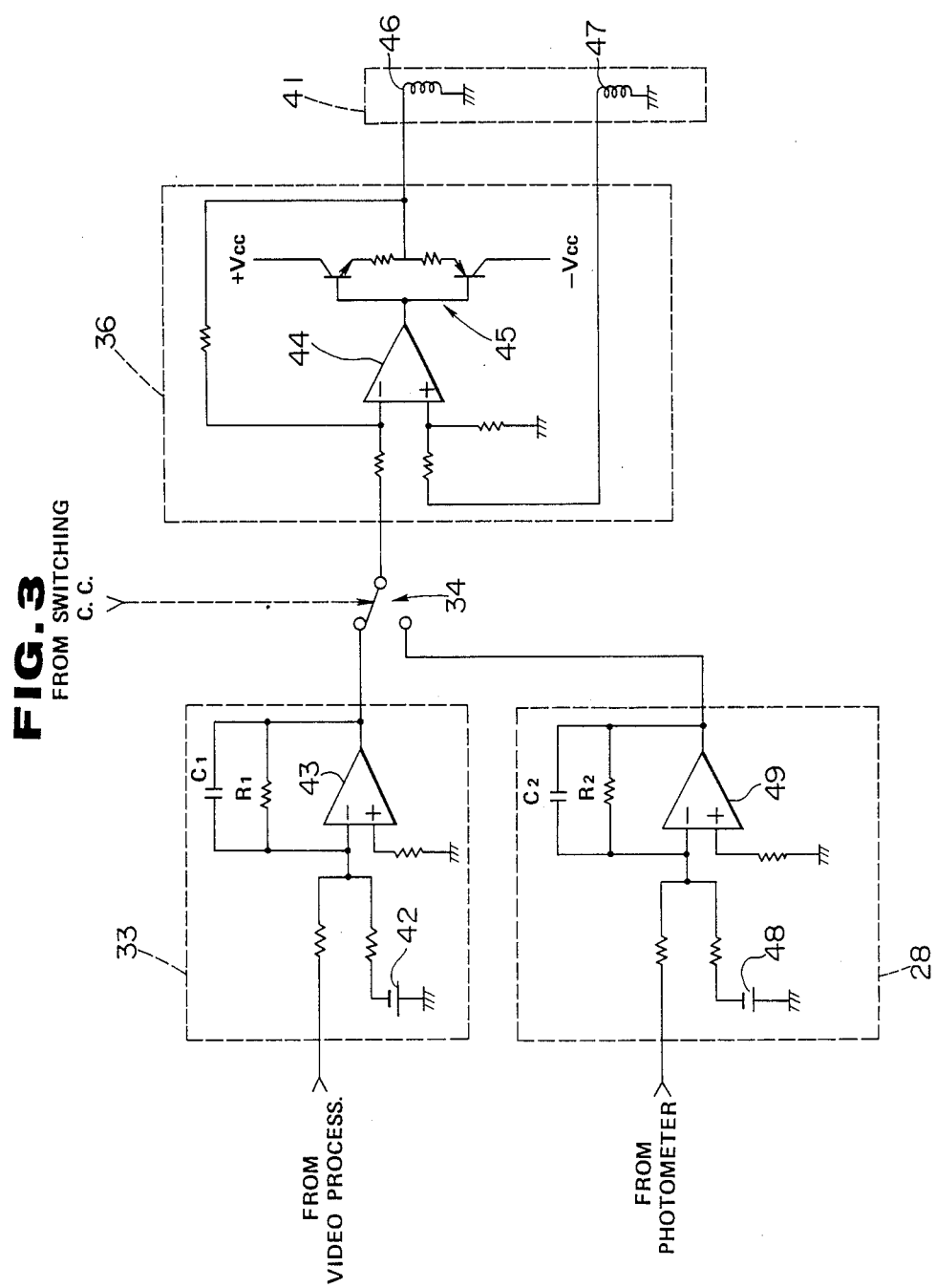

AUTOMATIC ADJUSTED LIGHT SWITCHING CIRCUIT

FIELD OF THE INVENTION

This invention relates to an endoscope light source apparatus which can feed the most suitable illuminating light in photographing and television imaging.

BACKGROUND OF THE INVENTION

An electron type endoscope (which shall be briefly mentioned as an electronic endoscope or electronic scope) wherein such solid state imaging device as a charge coupled device (abbreviated as CCD) is used instead of an image guide transmitting optical images is recently practiced so that an imaged endoscope picture image may be displayed on a TV monitor.

Also, a photographing camera (which shall be briefly mentioned as a still camera) is fitted to an eyepiece part of an optical endoscope (which shall be briefly mentioned as a fiber scope) wherein a conventional image guide is used so as to take a photograph or a TV camera containing such imaging means as a solid state imaging device is fitted to the same part so as to display a picture image on a TV monitor.

Now, the above mentioned electronic scope or fiber scope is used as connected to a light source apparatus feeding an illuminating light.

Conventionally, such light source apparatus is made in advance to be connected with a fiber scope so that, when a still camera is connected to the fiber scope, an iris will act so that the film surface illuminating degree may be constant and an automatic light adjustment will act. Therefore, even if the observing position varies, by the action of this automatic light adjustment, an object to be observed will be able to be observed by the observer always at a constant brightness. Further, the automatic light adjusting circuit is so designed that the responsiveness will be optimum when a still camera is connected.

However, it is in more cases that a TV camera is connected to a fiber scope and a picture image is observed on a TV monitor. For the light adjustment in such case, a video signal from the TV camera is input as an automatic light adjusting signal into the above mentioned automatic light adjusting circuit. However, this automatic light adjusting circuit corresponds to the still camera as mentioned above, therefore can not he said to be most suitable particularly in the responsiveness, for example, a hatching (the response is too early to be stable and flutters) and response delay (the response is too late to follow the variation of the brightness of the object) have occurred and such disadvantage that the observer is not only fatigued in the eye but also can not make a sufficient diagnosis has occurred. Further, in case an electronic scope is connected to one light source apparatus, the video signal from the electronic scope will be of the same kind as of the TV camera and, when it is connected to the automatic light adjusting circuit for the fiber scope, the same disadvantage as is mentioned above will occur.

OBJECT AND SUMMARY OF THE INVENTION

The present invention is made in view of the above mentioned circumstances and has it as an object to provide an endoscope light source apparatus whereby, even in case a photograph is taken with a still camera fitted to a fiber scope, even in case a monitor observation is made with a TV camera fitted to a fiber scope and even in case a monitor observation is made with an electronic scope, the most suitable responsiveness and light amount can be obtained and a clear photograph and an observed picture image easy to observe can be obtained.

The automatic adjusted light switching circuit of the present invention is provided with a video adjusted light controlling circuit and a still adjusted light controlling circuit outputting respectively a video controlling signal and still controlling signal which can adjust an iris. Either one of the these two controlling signals is selected by a switching circuit to be input into an iris driving circuit which drives the iris and controls the light amount.

The other features and advantages of the invention will become apparent enough with the following explanation.

BRIEF DESCRIPTION OF THE DRAWINGS

FIGS. 1 to 3 relate to the first embodiment of the present invention.

FIG. 1 is a block diagram explaining the formation of an entire endoscope apparatus.

FIG. 2 is a block diagram explaining the operation of a track switching circuit.

FIG. 3 is a circuit diagram of an endoscope light source apparatus.

DETAILED DESCRIPTION OF PREFERRED EMBODIMENTS

The embodiments of the present invention shall be explained in the following with reference to the drawings.

Figure 1:
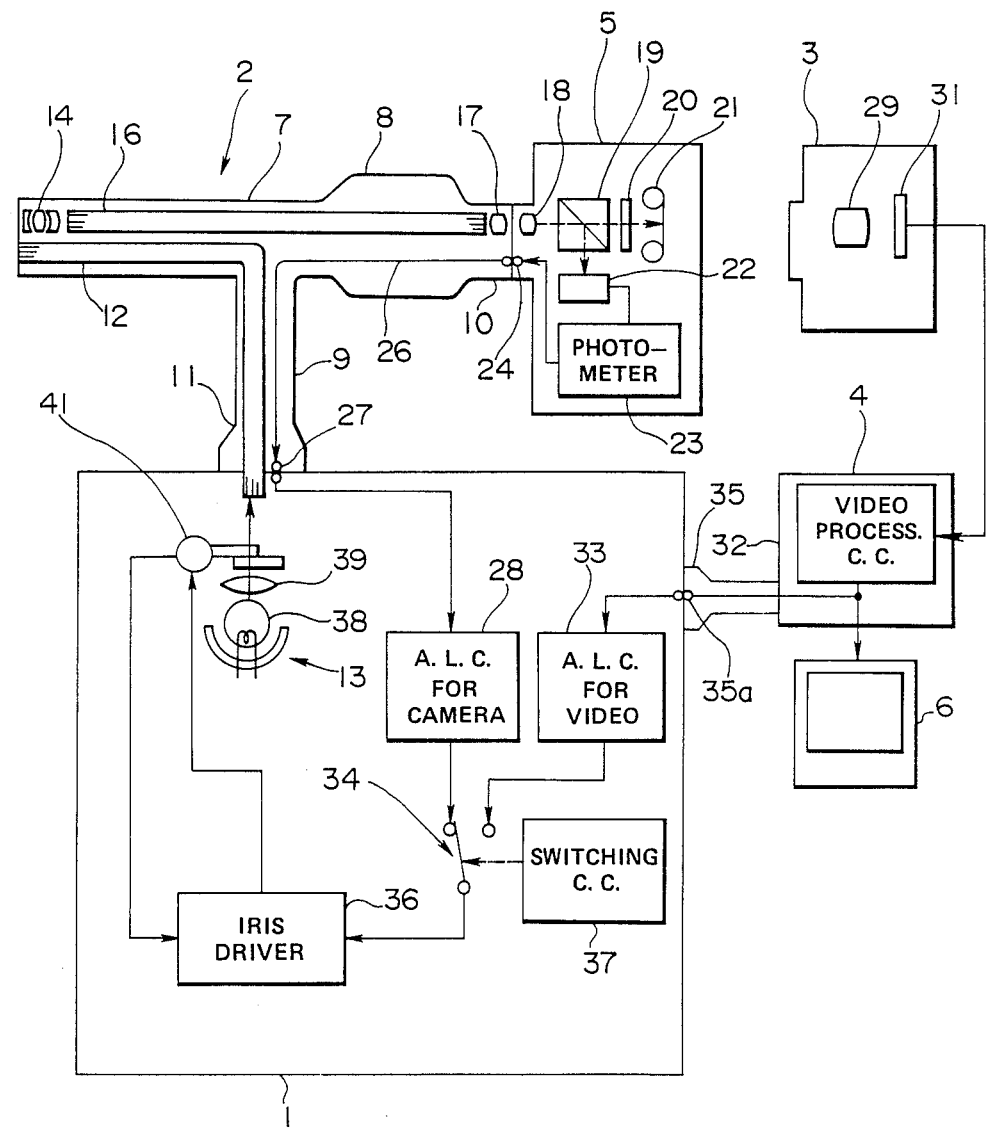

FIGS. 1 and 2 relate to the first embodiment of the present invention. FIG. 1 is an explanatory view of the formation of an entire endoscope apparatus. FIG. 2 is a circuit diagram of an endoscope light source apparatus.

In FIG. 1, an endoscope light source apparatus 1 can be connected to a fiber scope 2 removably fitted with an externally fitted still camera 5 and to a control apparatus 4 processing the signal of the output of an externally fitted TV camera 3. The control apparatus is to display an object image on a TV monitor 6.

The above mentioned fiber scope 2 has an elongate insertable part 7 and an operating part 8 connected to the rear end side of this insertable part 7. A universal cord 9 is extended from this operating part 8 and is provided at the tip with a light source connector 11. Further, an eye piece part 10 is provided at the rear end of the operating part 8.

A light guide 12 formed of a fiber bundle transmitting an illuminating light is inserted through the above mentioned insertable part 7. The illuminating light emitted from a light source part 13 within the above mentioned light source apparatus 1 is fed to the entrance end surface of this light guide 12, is transmitted to the exit end surface side and is projected out of this exit end surface to be able to illuminate the object side in the front.

An image forming objective lens 14 is arranged in the tip part of the above mentioned insertable part 7 so that the entrance end surface of an image guide 16 formed of a fiber bundle inserted together with the above mentioned light guide 12 through the insertable part 7 may be present in the image forming position of this objective lens 14. An eyepiece lens 17 is arranged as opposed to the exit end surface of this image guide 16 so that the observer can make a naked eye observation with this eyepiece lens 17 from the eyepiece part 10 fitted with the above mentioned externally fitted still camera 5. Within this externally fitted still camera 5, an image forming lens 18 and a beam splitter 19 in the rear of this imaging lens 18 are provided so that the optical axis may coincide with that of the above mentioned objective lens 17. A film 21 is arranged in the image forming position of this beam splitter 19 so as to receive the light transmitted through the beam splitter 19. A shutter 20 is interposed between this beam splitter 19 and the film 21 so as to be able to intercept the transmitted light. The reflected light by the beam splitter 19 enters such light receiving device 22 as, for example, a photodiode. The light entering this light receiving device 22 is photoelectrically converted and is input as a voltage signal into alight measuring circuit or photometer 23. From the photometer 23, the voltage signal is input as alight amount information signal into a still camera adjusted light controlling circuit 28 provided within the light source apparatus 1 through a terminal 24 provided in the eyepiece part 10, a transmitting line 26 inserted through the operating part 8 and universal cord 9 and a contact 27 provided in alight source connector 11.

On the other hand, within the externally fitted TV camera 3 which can be removably provided in the eyepiece part 10 of the fiber scope 2, an image forming lens 29 is provided so that the optical axis may coincide with that of the eyepiece lens 17 in case the TV camera 3 is fitted to the fiber scope 2. A solid state imaging device 31 is provided in the image forming position of this image forming lens 29 so as to form an object image entering through the image guide 16. The object image is photoelectrically converted by this solid state imaging device 31 and is input as an electric signal into a video signal processing circuit 32 within the above mentioned control apparatus 4. The input electric signal is processed by the video signal processing circuit 32 and is output as a composite video signal to the TV monitor 6 and the object image is displayed on the picture surface.

The composite video signal output from the above mentioned video signal processing circuit 32 is input into a video adjusted light controlling circuit 33 provided within the light source apparatus 1 through a contact 35a provided in a connector 35.

In the above mentioned still camera adjusted light controlling circuit 28 and video adjusted light controlling circuit 33, information signals relating to the light amounts and responses most suitable to the externally fitted still camera 5 and externally fitted TV camera 3 are produced and are input into an iris driving circuit 36 through a switching switch 34. This switching switch 34 is switched by a switching circuit 37 discriminating whether the endoscope connected tot he light source apparatus 1 is a fiber scope 2 or electronic scope or whether the camera fitted tot he fiber scope 2 is a still camera 5 or TV camera 3 so that, in case either of the electronic scope and externally fitted TV camera is used, the control signal of the video adjusted light controlling circuit 33 will be input into the iris driving circuit 36 and, in case the externally fitted still camera 5 is used, the control signal of the still camera adjusted light controlling circuit 28 will be input into the iris driving circuit 36.

FIG. 2 shows a concrete block diagram of the switching circuit 37.

Figure 2A:
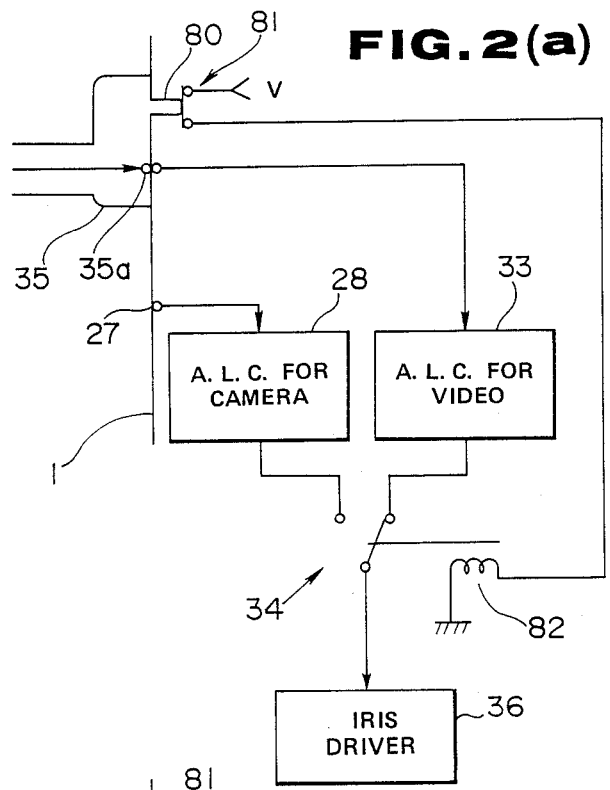
Figure 2B:
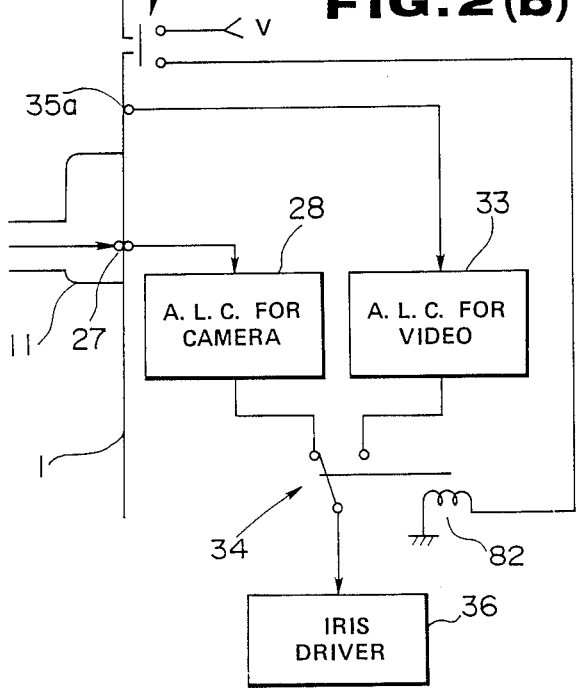

In FIG. 2(a), when the connector 35 of the control apparatus 4 is connected to the light source apparatus 1, a pin 80 provided on the end surface of the connector 35 will switch on a switch 81 provided in the light source apparatus 1 to excite a coil 82 forming the switching switch 34 which will be switched to the video adjusted light controlling circuit 33 side and a control signal will be delivered to the iris driving circuit 36. As in FIG. 2(b), in case the light source connector 11 of the fiber scope 2 is connected to the light source apparatus 1, as the connector 11 is not provided with the pin 80, the switch 81 will not be on and the coil 82 will not be excited. In case this switching switch 34 is not excited, it will be switched to the still camera adjusted light controlling circuit 28 and the control signal output from the still camera adjusted light controlling circuit 28 will be delivered to the iris driving circuit 36.

By the way, a manual switch may replace the switching circuit 37.

A condenser lens 39 and iris 41 re arranged on the light path connecting the entrance end surface of the light guide 12 of the above mentioned light source part 13 and the light source lamp 38. This iris 41 is driven by the control signal of the above mentioned iris driving circuit 36 so that the illuminating light emitted from the light source lamp 38 may be controlled to have the most suitable light amount and responsiveness.

In FIG. 3, the formation of the still camera adjusted light controlling circuit 28, video adjusted light controlling circuit 33 and iris driving circuit 36 shall be concretely explained.

The composite video signal processed by the video signal processing circuit 32 is input into the video adjusted light controlling circuit 33. This input signal is compared with a reference potential 42 by a comparator 43. Further, the responding speed is determined by a resistance R1 and condenser C1. The signal after the comparison and determination is input by the switching switch 34 into a comparator 44 within the iris driving circuit 36. The output of this comparator 44 is input into a driving coil 46 of an iris 41 through an output circuit 45 to drive the iris 41 provided with a braking coil 47. A braking signal is generated from this braking coil 47. The comparator 44 can stably drive the iris 41 with the difference between this braking signal and the input signal from the video adjusted light controlling circuit 33. On the other hand, in the case of using the still camera, the photometric signal from the photometer 23 is input into the still camera adjusted light controlling circuit 28. the input signal is compared with a reference potential 48 by a comparator 39 and further the responding speed is determined by a resistance R2 and condenser C2. The signal after the comparison and determination is input by the switching switch 34 into the comparator 44 within the iris driving circuit 36. The output of this comparator 44 is input into the driving coil 46 of the iris 41 through the output circuit 45 to drive the iris 41. By the way, the iris 41 is provided with the braking coil 47. A braking signal is generated from this braking coil 47. The comparator 44 can stably drive this iris 41 with the difference between this braking signal and the input signal from the video adjusted light controlling circuit 33.

In this case, the condenser C1 and resistance R1 are set at the time constant and gain most suitable to the externally fitted TV camera 3 and the condenser C2 and resistance R2 are set at the value most suitable to the photometric signal from the externally fitted still camera 5. The reference potentials 42 and 48 are set respectively for the externally fitted TV camera 3 and still camera 5 so that the illuminating light may be of the most suitable brightness.

By the above mentioned formation, even in case the externally fitted still camera 5 or TV camera 3 is fitted, the most suitable light amount and responsiveness can be omitted.

The reference potentials 42 and 48 may be made variable or a plurality of them may be provided to vary the light amount so that the brightness may be adjusted to be as desired by the user. Further, the above mentioned operation may be made by an instruction from a microcomputer. In such case, the brightness desired by the user may be memorized in the microcomputer.

Figure 4:
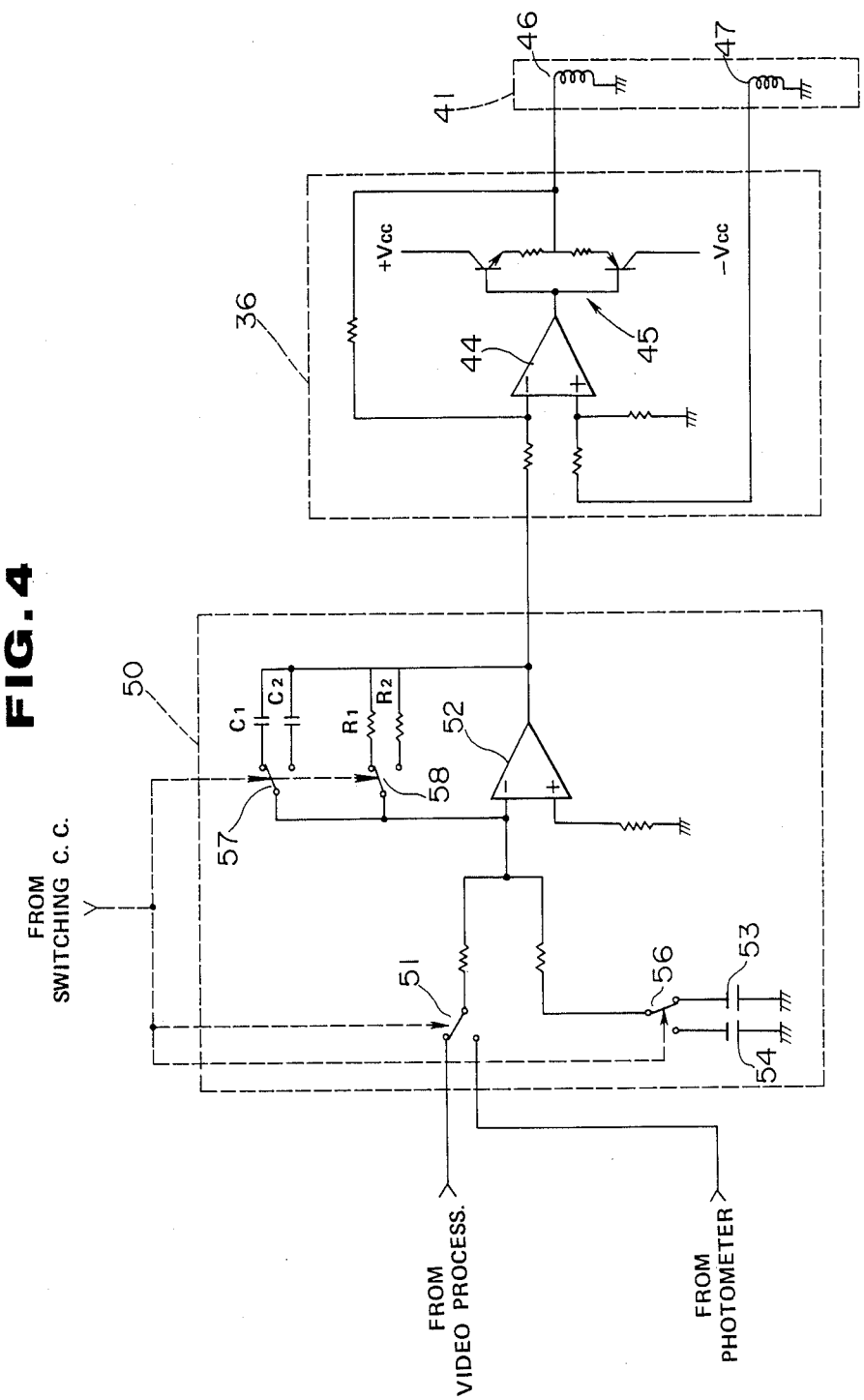
FIG. 4 relates to the second embodiment of the present invention and is a circuit diagram of an endoscope light source apparatus.

FIG. 4 shows the second embodiment of the present invention.

In this embodiment, the adjusted light controlling circuit of the first embodiment is used for both of the externally fitted still camera 5 and TV camera 3.

The video signal from the externally fitted TV camera 3 and the photometric signal from the externally fitted still camera are selected by a switching switch 51 and the video signal is input into a comparator 52 within an adjusted light controlling circuit 50. A reference potential 53 corresponding to the most suitable light amount of the externally fitted TV camera 3 and a reference potential 54 corresponding to the most suitable light amount of the externally fitted still camera 5 are selected by a switching switch 56. The selected reference potential 53 and the video signal are compared by the operator. This comparator 52 is connected with the condenser C1 and resistance R1 determining the responding speed most suitable to the externally fitted TV camera 3 and the condenser C2 and resistance R2 determining the responding speed most suitable tot he externally fitted still camera 5 through switching switches 57 and 58 by which the condenser C1 and resistance R1 are selected so that information signals of the light amount and responding speed most suitable to the externally fitted TV camera 3 may be input into the iris driving circuit 36 from the comparator 52.

By the way, the switching switches 51, 56 and 58 are controlled by the switching circuit.

In this embodiment, as compared with the first embodiment, the number of the costly comparators can be reduced and therefore the cost can be reduced.

The other formations, operations and effects are the same as in the first embodiment.

In the above mentioned respective embodiments the fiber scope fitted with the externally fitted TV camera or still camera has been described but an electronic scope may be connected instead of the externally fitted TV camera.

As explained above, according to the present invention, even in the case of photographing with a still camera fitted to a fiber scope, of monitor-observing with a TV camera, fitted to a fiber scope or of monitor-observing with an electronic scope, the optimum responsiveness and light amount can be obtained and a clear photograph and an observed picture image easy to observe can be obtained.

In this invention, it is apparent that working modes different in a wide range can be formed on the basis of this invention without departing from the spirit and scope of the invention. This inventions is not restricted by its specific working mode except being limited by the appended claims.

What is claimed is:

1. An automatic adjusted light switching circuit comprising:
   a light source emitting an illuminating light to illuminate an object;
   a light amount controlling means capable of controlling the light amount of said light source;
   a first light adjusting means capable of outputting a control signal which can adjust said light amount controlling means with an information signal relating to the brightness of said object;
   a second light adjusting means capable of outputting a control signal having a light adjusting characteristic different from that of the first light adjusting means from a video signal obtained from a solid state imaging device by imaging said object image with said solid state imaging device; and
   a selecting means capable of selecting the control signals output from said first light adjusting means and second light adjusting means and of inputting into said light amount controlling means the control signal output from either one.

2. An automatic adjusted light switching circuit according to claim 1 wherein said first light adjusting means is a still camera light adjusting means capable of outputting a control signal by inputting a photometric signal including an information relating to the illumination intensity of the object image formed on a photographic film fitted to the still camera.

3. An automatic adjusted light switching circuit according to claim 1 wherein said second light adjusting means is a video light adjusting means capable of outputting a control signal which can adjust the light amount of said light source to make the brightness most suitable to the input video signal.

4. An automatic adjusted light switching circuit according to claim 2 wherein said still camera light adjusting means has a comparator comparing the reference potential and photometric signal.

5. An automatic adjusted light switching circuit according to claim 3 wherein said video light adjusting means has a comparator comparing the reference potential and video signal.

6. An automatic adjusted light switching circuit according to claim 1 wherein said first light adjusting means and second light adjusting means are integral, are formed of the same comparator and selectively perform the functions as of said first light adjusting means and second light adjusting means by selecting a plurality of electric parts connected to said comparator.

* * * * *